US011950859B2

(12) United States Patent
Zhang et al.

(10) Patent No.: US 11,950,859 B2
(45) Date of Patent: Apr. 9, 2024

(54) NAVIGATION AND POSITIONING SYSTEM AND METHOD FOR JOINT REPLACEMENT SURGERY ROBOT

(71) Applicant: BEI JING LONGWOOD VALLEY MEDICAL TECHNOLOGY CO. LTD, Beijing (CN)

(72) Inventors: Yiling Zhang, Beijing (CN); Xingyu Liu, Beijing (CN)

(73) Assignees: Beijing Longwood Valley Medical Technology CO. LTD. (CN); Yiling Zhang (CN)

( * ) Notice: Subject to any disclaimer, the term of this patent is extended or adjusted under 35 U.S.C. 154(b) by 0 days.

(21) Appl. No.: 18/258,160

(22) PCT Filed: Jan. 22, 2021

(86) PCT No.: PCT/CN2021/073209
§ 371 (c)(1),
(2) Date: Jun. 16, 2023

(87) PCT Pub. No.: WO2022/126827
PCT Pub. Date: Jun. 23, 2022

(65) Prior Publication Data
US 2024/0065771 A1 Feb. 29, 2024

(30) Foreign Application Priority Data

Dec. 18, 2020 (CN) .......................... 202011506573.3

(51) Int. Cl.
*A61B 34/20* (2016.01)
*A61B 34/10* (2016.01)
*A61B 34/30* (2016.01)

(52) U.S. Cl.
CPC .............. *A61B 34/20* (2016.02); *A61B 34/10* (2016.02); *A61B 34/30* (2016.02); *A61B 2034/105* (2016.02); *A61B 2034/2055* (2016.02)

(58) Field of Classification Search
CPC ..................................... A61B 34/20–2034/258
See application file for complete search history.

(56) References Cited

U.S. PATENT DOCUMENTS

| 2005/0281465 A1 | 12/2005 | Marquart et al. |
| 2007/0073133 A1 | 3/2007 | Schoenefeld |
| 2016/0128654 A1 | 5/2016 | Wollowick et al. |
| 2019/0321126 A1 | 10/2019 | Otto et al. |
| 2020/0197105 A1 | 6/2020 | Wu |

FOREIGN PATENT DOCUMENTS

| CN | 105025835 A | 11/2015 |
| CN | 107468351 A | 12/2017 |

(Continued)

OTHER PUBLICATIONS

International Search Report and Written Opinion for corresponding International application No. PCT/CN2021/073209; dated Sep. 1, 2021 (19 pages) Machine Translation.

(Continued)

*Primary Examiner* — Zade Coley
(74) *Attorney, Agent, or Firm* — Mendelsohn Dunleavy, P.C.

(57) ABSTRACT

The present application provides a joint replacement surgical robot navigation and positioning system and method. The system includes a preoperative planning module, which is used to: perform segmentation and reconstruction for a hip joint to obtain a three-dimensional model of the hip joint according to obtained medical image data of the hip joint, and carry out a preoperative planning to determine a surgical scheme according to the three-dimensional model of the hip joint; an optical navigation and positioning module, which is used to: generate a navigation instruction according to the surgical scheme, register the three-dimensional model of the hip joint to obtain a hip joint entity model according to spatial position relationships among an optical positioning device, a hip joint of a patient and a surgical probe, match the hip joint entity model with the preoperative planning model, and determine a surgical position on a bone of the patient according to the hip joint entity model; and a mechanical arm control module, which is used to: move an (Continued)

end effector to the surgical position on the bone of the patient, and control the end effector to perform osteotomy, rasion, and press-fitting operations on the hip joint according to the navigation instruction. Preoperative planning is executed through the orthopedic surgical robot, surgical operation is completed at a high level, the operation intensity of surgeons may be greatly reduced, the operation time is saved, and the operation accuracy is improved.

10 Claims, 9 Drawing Sheets

(56) References Cited

FOREIGN PATENT DOCUMENTS

| | | |
|---|---|---|
| CN | 108778179 A | 11/2018 |
| CN | 109890281 A | 6/2019 |
| CN | 110974426 A | 4/2020 |
| CN | 111179350 A | 5/2020 |
| CN | 111345895 A | 6/2020 |
| CN | 111467036 A | 7/2020 |

OTHER PUBLICATIONS

First Office Action for corresponding Chinese application No. 202011506573.3; dated Jun. 17, 2021 (21 pages) Machine Translation.

NAVIGATION AND POSITIONING SYSTEM AND METHOD FOR JOINT REPLACEMENT SURGERY ROBOT

CROSS-REFERENCE TO RELATED APPLICATION

The present application claims priority to Chinese patent application No. 2020115065733 filed on Dec. 18, 2020, entitled "Navigation and Positioning System and Method for Joint Replacement Surgery Robot", which is hereby incorporated by reference in its entirety.

FIELD

The present application relates to the field of medical instrument, and in particular, to a navigation and positioning system and method for a joint replacement surgical robot.

BACKGROUND

In recent years, hip joint replacement, as an effective treatment solution for hip joint diseases, has been widely developed. Hip joint disease is a disease with high incidence rate in China, and there may be nearly ten million new patients having various hip joint related diseases in Asia. Traditional joint replacement surgery lacks comprehensive preoperative planning, sufficient preoperative preparation and accurate intraoperative navigation and positioning, and heavily relies on surgeon's personal experience, and the operations of the traditional joint replacement surgery are cumbersome and have poor repeatability, resulting in a high incidence rate of postoperative complications, which seriously restricts an effectiveness of hip joint replacement surgery.

SUMMARY (1) Problems to be Solved

In view of the above problems, embodiments of the present application provide a navigation and positioning system and method for a joint replacement surgical robot.

(2) Summary An embodiment of the present application provides a navigation and positioning system for a joint replacement surgical robot, including: a preoperative planning module, an optical navigation and positioning module and a mechanical arm control module;

where the preoperative planning module is configured to perform, based on medical image data of a hip joint, segmentation and reconstruction for the hip joint to obtain a three-dimensional model of the hip joint, and perform, based on the three-dimensional model of the hip joint, a preoperative planning to determine a surgical scheme;

the optical navigation and positioning module is configured to generate a navigation instruction based on the surgical scheme, register the three-dimensional model of the hip joint based on spatial position relationships between an optical positioning device, a hip joint of a patient and a surgical probe to obtain a hip joint entity model, match the hip joint entity model with a preoperative planed model, and determine a surgical position on a bone of the patient based on the hip joint entity model; and the mechanical arm control module is configured to move an end effector to the surgical position on the bone of the patient, and control the end effector to perform osteotomy operation, rasion operation, and press-fitting operation on the hip joint based on the navigation instruction.

In an embodiment of the present application, the preoperative planning module includes: a data obtaining submodule, a three-dimensional model reconstruction submodule, an acetabular side plan determination submodule, a femoral side plan determination submodule and a plan scheme confirmation submodule;

where the data obtaining submodule is configured to obtain the medical image data of the hip joint;

the three-dimensional model reconstruction submodule is configured to perform, based on the medical image data of the hip joint, segmentation and reconstruction for the hip joint to obtain the three-dimensional model of the hip joint;

the acetabular side plan determination submodule is configured to determine an acetabulum rotation center, an acetabulum diameter, an acetabulum anteversion angle and an acetabulum abduction angle based on the three-dimensional model of the hip joint, and determine a size and a position of an acetabular side prosthesis based on the acetabulum rotation center, the acetabulum diameter, the acetabulum anteversion angle and the acetabulum abduction angle when considering an acetabular shell coverage rate;

the femoral side plan determination submodule is configured to determine a caput femoris rotation center, a femur marrow cavity shape, a femur marrow cavity anatomical axis and a femur collodiaphyseal angle based on the three-dimensional model of the hip joint, and determine a size and a position of a femoral side prosthesis based on the caput femoris rotation center, the femur marrow cavity shape, the femur marrow cavity anatomical axis and the femur collodiaphyseal angle when considering a leg length difference and a femoral combined offset;

and the plan scheme confirmation submodule is configured to confirm whether an acetabular side prosthesis implantation plan determined by the acetabular side plan determination submodule and a femoral side prosthesis implantation plan determined by the femoral side plan determination submodule are suitable; in case that the acetabular side prosthesis implantation plan determined by the acetabular side plan determination submodule or the femoral side prosthesis implantation plan determined by the femoral side plan determination submodule is not suitable, the acetabular side plan determination submodule and/or the femoral side plan determination submodule are triggered to re-determine an acetabular side prosthesis implantation plan and a femoral side prosthesis implantation plan; and in case that the acetabular side prosthesis implantation plan determined by the acetabular side plan determination submodule and the femoral side prosthesis implantation plan determined by the femoral side plan determination submodule are suitable, the acetabular side prosthesis implantation plan determined by the acetabular side plan determination submodule and the femoral side prosthesis implantation plan determined by the femoral side plan determination submodule are used as preoperative planning schemes.

In an embodiment of the present application, the optical navigation and positioning module is configured to:

determine a spatial position of the hip joint of the patient based on a pelvic reference frame and a femoral reference frame, register the three-dimensional model of the hip joint, based on a spatial position relationship between the hip joint of the patient and a mechanical arm to obtain the hip joint entity model, and determine the surgical position on the bone of the patient and a real-time position and posture of the mechanical arm based on the hip joint entity model. In an embodiment of the present application, the optical navigation and positioning module includes an optical tracking submodule;

the optical tracking submodule is configured to register the hip joint entity model based on a spatial position relationship between the mechanical arm and the pelvic reference frame and the femoral reference frame, and calibrate a position of a mechanical arm model based on a registered hip joint entity model.

In an embodiment of the present application, in case that the optical tracking submodule registers the hip joint entity model based on the spatial position relationship between the mechanical arm and the pelvic reference frame and the femoral reference frame, the optical tracking submodule is configured to:

use a triangle as a minimum unit in a registration process, and in case that points marked by a surgeon during a surgery are A, B and C, corresponding preoperative planed points are a, b and c, where the points marked by the surgeon are on a surface of human tissue;

select a', b' and c' from neighborhood space point sets corresponding to a, b and c, where all three points a', b' and c' are on the surface of human tissue, and a triangle a'b'c' composed of the three points a', b' and c' and a triangle composed of the three points A, B and C are congruent triangles; and correct preoperative planed spatial positions of a, b and c to spatial positions of a', b' and c', and register the points marked during the surgery and the preoperative planed points by using a registration mode to achieve accurate registration for a femoral side surface and an acetabular side surface.

In an embodiment of the present application, the mechanical arm control module includes a mechanical arm position positioning submodule;

the mechanical arm position positioning submodule is configured to send position and posture information of the mechanical arm to the optical tracking submodule to make the optical tracking submodule obtain spatial position information of the mechanical arm in real time.

In an embodiment of the present application, in case that the mechanical arm control module performs a rasion operation, the mechanical arm control module is configured to:

determine a safe operating range and a conical stereotactic boundary;

when an operation position of the mechanical arm exceeds the safe operating range, control force exertion to generate the conical stereotactic boundary to control the mechanical arm to rasp within the conical stereotactic boundary;

where the conical stereotactic boundary appears when an acetabular rasp moves close to a planned position of an acetabular shell in an acetabulum, the boundary is designed to be of a conical shape; when the acetabular rasp moves close to a target position, a cross section of the boundary is displayed to restrict the mechanical arm; when the acetabular rasp deviates from the conical stereotactic boundary, the acetabular rasp is guided back inside the conical stereotactic boundary; when the mechanical arm is used within the conical stereotactic boundary, the mechanical arm completes an operation according to an coaxial within a positioning control range, where the mechanical arm supports power to complete high-speed rasion operations; in case that the mechanical arm moves beyond the conical stereotactic boundary by a preset angle, an electric source of the acetabular rasp is cut off to stop the rasion operation.

In an embodiment of the present application, in case that the mechanical arm control module performs a press-fitting operation, the mechanical arm control module is configured to:

in case that the press-fitting operation is performed on the acetabulum and a pressing-fitting rod is moved into the acetabulum, the conical stereotactic boundary starts, the anteversion angle and the abduction angle are aligned in real time to make the anteversion angle and the abduction angle match with preoperative planed anteversion angle and abduction angle, and a matching effect is displayed;

where the press-fitting operation is stopped when a distance between a head end of the acetabular rasp and a target depth is 0 mm in each direction of an upper and lower direction, an inner and outer direction and a forward and backward direction, while a press-fitting map and the conical stereotactic boundary are updated; and real-time monitoring of whether the patient moves during the press-fitting operation is performed, and in case that the patient moves, the mechanical arm performs position compensation in real time, and a guidance is provided to assist in completing the operation in a compensation mode.

In an embodiment of the present application, the navigation and positioning system further includes: a display module;

the display module is communicated with the optical navigation and positioning module and configured to display a real-time status of the hip joint entity model on a human-computer interactive display screen.

In an embodiment of the present application, the optical navigation and positioning module collects spatial positions of at least three mark points on the bone of the patient through the surgical probe, registers the three-dimensional model of the hip joint based on spatial position relationships between the at least three mark points on the bone of the patient and the hip joint of the patient to obtain the hip joint entity model.

In an embodiment of the present application, the optical navigation and positioning module further includes: a postoperative verification submodule;

the postoperative verification submodule is configured to, after the three-dimensional model of the hip joint is registered, collect spatial positions of at least three mark points on the bone of the patient again through the surgical probe, and verify that whether registered positions of the mark points are correct.

An embodiment of the present application provides a navigation and positioning method for a joint replacement surgical robot, including:

performing, based on medical image data of a hip joint, segmentation and reconstruction for the hip joint to obtain a three-dimensional model of the hip joint, and performing, based on the three-dimensional model of the hip joint, a preoperative planning to determine a surgical scheme;

generating a navigation instruction based on the surgical scheme, registering the three-dimensional model of the hip joint based on spatial position relationships between an optical positioning device, a hip joint of a patient and a surgical probe to obtain a hip joint entity mode, matching the hip joint entity model with a preoperative planed model, and determining a surgical position on a bone of the patient based on the hip joint entity model; and moving an end effector to the surgical position on the bone of the patient, and controlling the end effector to perform osteotomy operation, rasion operation, and press-fitting operation on the hip joint based on the navigation instruction.

An embodiment of the present application provides an electronic device including a memory, a processor and a computer program stored on the memory and executable by the processor, where the processor executes the computer program to make the electronic device implement the steps of the above navigation and positioning method for a joint replacement surgical robot.

(3) Beneficial Effect

Embodiments of the present application provide a navigation and positioning system and method for a joint replacement surgical robot. Before the surgery, the 3D model of the hip joint is obtained based on the medical image data of the hip joint, and then preoperative planning is performed based on the 3D model of the hip joint to determine the surgical scheme. During the surgery, the navigation instruction is generated according to the surgical scheme, and the 3D model of the hip joint is registered based on the spatial position relationship between the hip joint of the patient and the surgical probe, therefore a structure of the hip joint of the patient may be accurately reflected through the 3D model of the hip joint, so that the surgical position on the bone of the patient may be accurately located, and the surgical robot may perform surgical operations according to the navigation instruction and surgical position. It can be seen from the above-mentioned description that the embodiments of the present application uses the 3D model for preoperative planning, uses the spatial positioning methods for intraoperative navigation and positioning, so that the surgical robot may optimize surgical path planning by using the high-accuracy 3D model, and realize the surgical path through a high degree of freedom mechanical arm, thereby assisting orthopedic surgeons in completing operations such as osteotomy, grinding, and fixation.

BRIEF DESCRIPTION OF THE DRAWINGS

In order to clearly illustrate the solutions disclosed in the embodiments of the present application, the drawings used in the descriptions of the embodiments are briefly described below. The drawings in the following description are only certain embodiments of the present application, and other drawings may be obtained according to these drawings without creative work for those skilled in the art.

DETAILED DESCRIPTION

The embodiments of the present application are described in conjunction with the accompanying drawings. The following embodiments are only used to provide a clearer illustration for the solutions of the present application, and cannot be used to limit the scope of protection of the present application.

Figure 1:
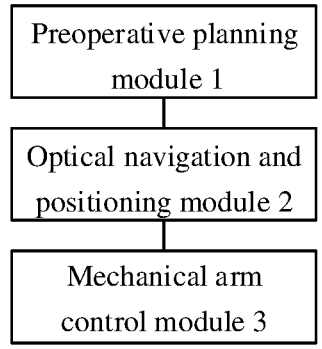
FIG. 1 is a schematic structural diagram of a navigation and positioning system for a joint replacement surgical robot according to an embodiment of the present application.

FIG. 1 is a schematic structural diagram of a navigation and positioning system for a joint replacement surgical robot according to an embodiment of the present application. The navigation and positioning system for the joint replacement surgical robot according to the embodiment of the present application is illustrated in detail below in combination with the FIG. 1.

As shown in FIG. 1, the navigation and positioning system for the joint replacement surgical robot according to the embodiment of the present application includes a preoperative planning module 1, an optical navigation and positioning module 2 and a mechanical arm control module 3.

The preoperative planning module 1, is used to perform, based on medical image data of a hip joint, segmentation and reconstruction for the hip joint to obtain a three-dimensional model of the hip joint, and perform, based on the three-dimensional model of the hip joint, a preoperative planning to determine a surgical scheme.

The optical navigation and positioning module 2, is used to generate a navigation instruction based on the surgical scheme, register the three-dimensional model of the hip joint based on spatial position relationships between an optical positioning device, a hip joint of a patient and a surgical probe to obtain a hip joint entity model, match the hip joint entity model with a preoperative planed model, and determine a surgical position on a bone of the patient based on the hip joint entity model.

The mechanical arm control module 3, is used to move an end effector to the surgical position on the bone of the patient, and control the end effector to perform osteotomy operation, rasion operation, and press-fitting operation on the hip joint based on the navigation instruction.

In the embodiment, preoperative scanning on pelvis and lower limbs of a patient may be performed by using imaging devices (such as CT/MRI/X-ray) to generate a preoperative three-dimensional (3D) view of the pelvis and lower limbs. In an embodiment, before a surgery, the surgical navigation system reads a CT image with a DICOM format, segments a hip joint image to obtain multiple segmented images, and reconstructs, based on image data corresponding to the multiple segmented images, an individualized complex 3D model of the hip joint, where the 3D model of the hip joint includes a virtual pelvis and femur, which makes the surgeon comprehensively evaluate preoperative conditions of the patient through the 3D model of the hip joint, plan the surgical scheme using a system software, and simulate the surgical scheme for the hip joint (femoral and acetabular sides). The surgical scheme includes surgical information of an implanted prosthesis, such as a position, a size and an angle. In the embodiment of the present application, a medical image processing may be implemented on a common computer, and surgeons may arbitrarily divide visualized 3D images. In the surgical navigation system, lesion information is clearly visible and easy to surgical operation.

In the embodiment, the surgical navigation system is loaded into a computer system, which includes measuring acetabular shape, bone mass, acetabular abduction angle, acetabular anteversion angle, leg length difference and femoral combined offset. During the surgery, all data may be templated based on actual measurement data and displayed on the computer in time to determine the size and position of the prosthesis.

Figure 7:
FIG. 7 is a schematic diagram of an acetabular shell implantation plan using a navigation and positioning system for a joint replacement surgical robot according to an embodiment of the present application.
Figure 8:
FIG. 8 is a schematic diagram of a femoral stem implantation plan using a navigation and positioning system for a joint replacement surgical robot according to an embodiment of the present application.
Figure 9:
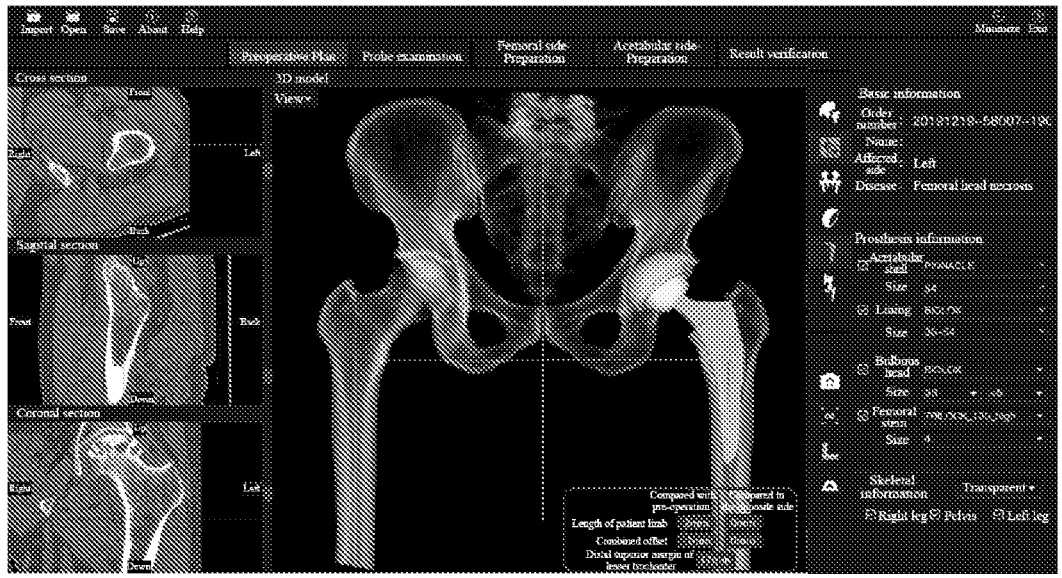
FIG. 9 is a schematic diagram of an osteotomy operation using a navigation and positioning system for a joint replacement surgical robot according to an embodiment of the present application.
Figure 10:
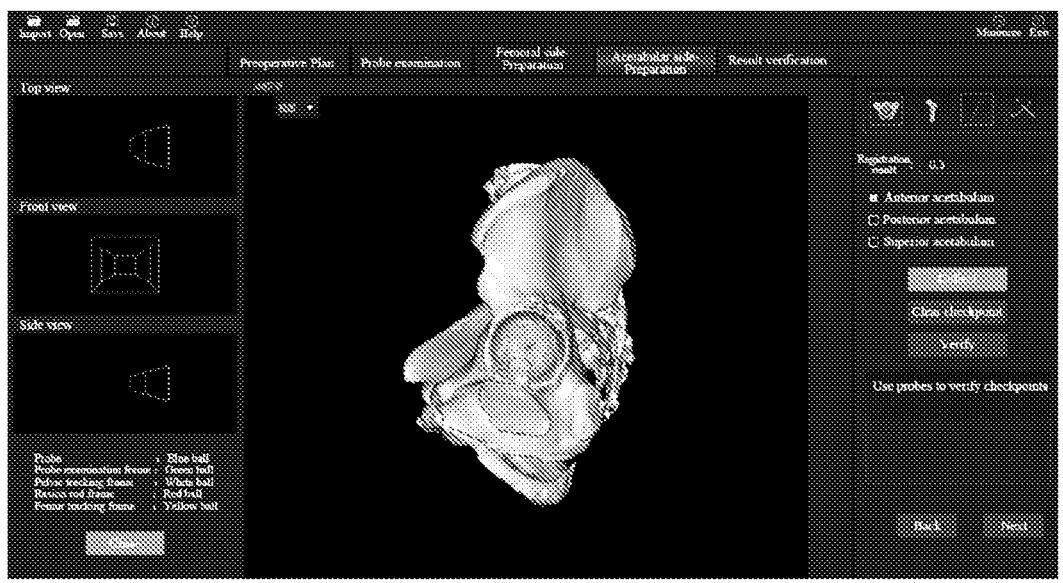
FIG. 10 is a schematic diagram of a rasion operation using a navigation and positioning system for a joint replacement surgical robot according to an embodiment of the present application.
Figure 11:
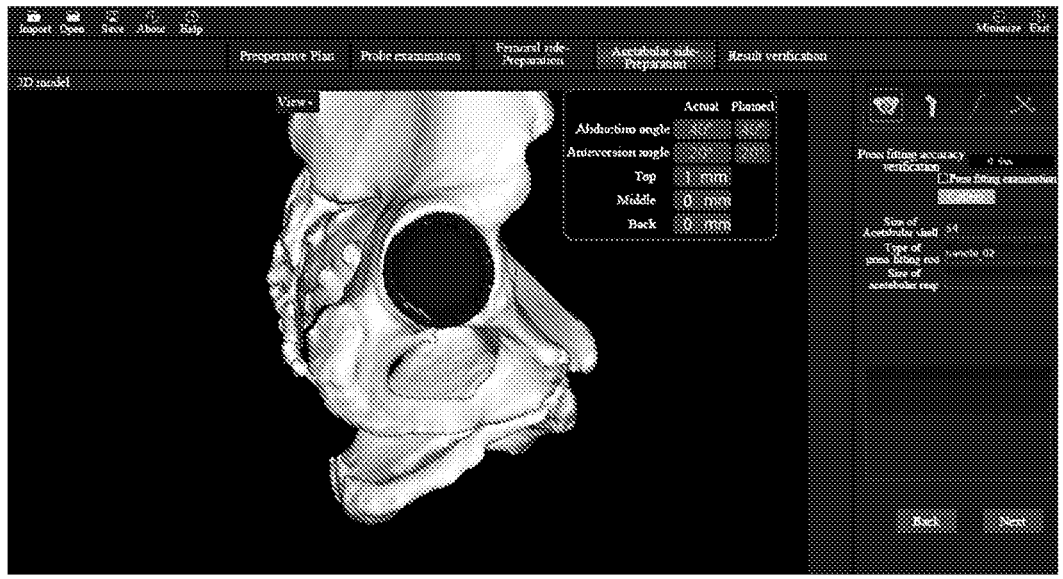
FIG. 11 is a schematic diagram of a press-fitting operation using a navigation and positioning system for a joint replacement surgical robot according to an embodiment of the present application.

In the embodiment, FIG. 7 illustrates a schematic diagram of an acetabular shell implantation plan using a navigation and positioning system for a joint replacement surgical robot according to an embodiment of the present application, and FIG. 8 illustrates a schematic diagram of a femoral stem implantation plan using a navigation and positioning system for a joint replacement surgical robot according to an embodiment of the present application. As shown in FIGS. 7 and 8, determining prosthesis plantation scheme in preoperative planning includes: simulating actual situations of an implanted acetabular shell and femoral stem, and displaying information associated with the prosthesis.

In the embodiment, pelvic reference frame and femoral reference frame may be manually placed on the acetabular side and femoral side respectively, and tracer elements on the pelvic reference frame and femoral reference frame may be tracked by using a navigation camera of the system to determine spatial positions of the pelvis and femur of the hip joint of the patient. Correspondingly, in case that the surgical probe collects points, the navigation camera tracks a tracer element at a tail of the surgical probe, calculates spatial positions of the collected points through an algorithm, and then integrates the spatial positions of the surgical probe, pelvic reference frame, and femoral reference frame into a common coordinate system to register the 3D model of the hip joint. At this time, the corresponding collection points may be displayed in the 3D model of the hip joint, and accurate registration for the femoral side surface and acetabular side surface may be achieved through a point cloud registration algorithm. The optical navigation and positioning module 2 registers intraoperative patient position and preoperative scanning data (such as CT and MRI) in a coordinate system to find a conversion relationship between the preoperative scanning data and the intraoperative patient position, and then the 3D model of the hip joint generated in the preoperative plan may be corrected based on the intraoperative patient position to reduce spatial position errors of mark points in the preoperative planning process, thereby greatly improving the registration accuracy.

According to contents of the above-mentioned embodiments, in an embodiment, the preoperative planning module includes: a data obtaining submodule, a three-dimensional model reconstruction submodule, an acetabular side plan determination submodule, a femoral side plan determination submodule and a plan scheme confirmation submodule.

The data obtaining submodule is used to obtain the medical image data of the hip joint.

The three-dimensional model reconstruction submodule is used to perform, based on the medical image data of the hip joint, segmentation and reconstruction for the hip joint to obtain the three-dimensional model of the hip joint.

The acetabular side plan determination submodule is used to determine an acetabulum rotation center, an acetabulum diameter, an acetabulum anteversion angle, and an acetabulum abduction angle based on the 3D model of the hip joint, and determine a size and a position of the acetabular side prosthesis based on the acetabulum rotation center, the acetabulum diameter, the acetabulum anteversion angle and the acetabulum abduction angle when considering an acetabular shell coverage rate.

For example, in case that the acetabular diameter of the 3D model of the hip joint is 50 mm, the corresponding size of the acetabular side prosthesis is determined to be about 50 mm; in case that the acetabulum anteversion angle is 20°, the acetabulum abduction angle is 40°, and then the position of the acetabular prosthesis is determined based on the position of the acetabulum rotation center and a rule that the acetabular shell coverage rate is greater than 70%.

The femoral side plan determination submodule is used to determine, based on the three-dimensional model of the hip joint, a caput femoris rotation center, a femur marrow cavity shape, a femur marrow cavity anatomical axis and a femur collodiaphyseal angle, and determine a size and a position of the femoral side prosthesis based on the caput femoris rotation center, the femur marrow cavity shape, the femur marrow cavity anatomical axis and the femur collodiaphyseal angle when considering a leg length difference and a femoral combined offset.

In an embodiment, a rotation center of the femoral side prosthesis may be determined based on the caput femoris rotation center; an axis of the femoral side prosthesis may be determined based on the femur marrow cavity anatomical axis; and the size of the femoral side prosthesis may be determined based on the femur marrow cavity shape and the femur collodiaphyseal angle.

The plan scheme confirmation submodule is used to confirm whether an acetabular side prosthesis implantation plan determined by the acetabular side plan determination submodule and a femoral side prosthesis implantation plan determined by the femoral side plan determination submodule are suitable; in case that the acetabular side prosthesis implantation plan determined by the acetabular side plan determination submodule or the femoral side prosthesis implantation plan determined by the femoral side plan determination submodule is not suitable, the acetabular side plan determination submodule and/or the femoral side plan determination submodule are triggered to re-determine an acetabular side prosthesis implantation plan and a femoral side prosthesis implantation plan; and in case that the acetabular side prosthesis implantation plan determined by the acetabular side plan determination submodule and the femoral side prosthesis implantation plan determined by the femoral side plan determination submodule are suitable, the acetabular side prosthesis implantation plan determined by the acetabular side plan determination submodule and the femoral side prosthesis implantation plan determined by the femoral side plan determination submodule are used as preoperative planning schemes.

In the embodiment, the confirm whether the acetabular side prosthesis implantation plan determined by the acetabular side plan determination submodule and the femoral side prosthesis implantation plan determined by the femoral side plan determination submodule are suitable includes: confirm whether the size of the acetabular side prosthesis is suitable based on a rule that a diameter of the acetabular shell is approximately equal to the diameter of the acetabulum, the acetabular shell fits with an anterior and posterior diameter of the acetabulum without excessive bone wear, and the acetabular shell coverage rate is greater than 70%; confirm whether the position of the acetabular shell is suitable based on a rule that the acetabular shell is in a safe area; and confirm whether the femur is suitable based on a rule that the femoral side prosthesis fits in the femur.

In an embodiment of the present application, the point cloud selected from the scanning data before the surgery is fitted with the point cloud marked by a surgeon in the surgery to find a most appropriate rotation matrix. The points marked by the surgeon on a patient body may refer to the points selected before the surgery. In case that the points marked by the surgeon and the points selected before the surgery are not in the same positions on the patient body, it is necessary to adjust the position of the point cloud selected before the surgery in real time based on a spatial position relationship and a structure of the point cloud marked by the surgeon, to make the final registration results have high accuracy. The point cloud registration algorithm is as follows.

Figure 14:
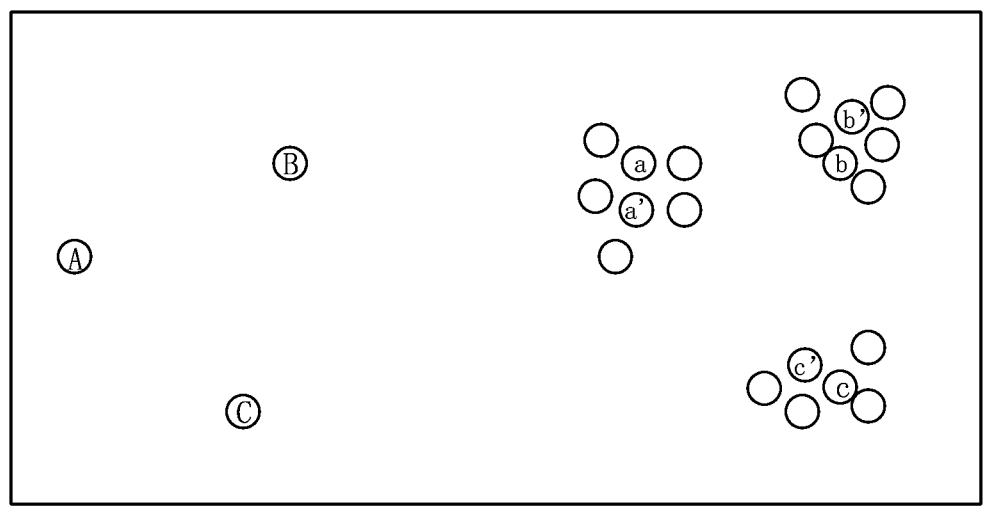
FIG. 14 is a schematic diagram of a registration process of a navigation and positioning system for a joint replacement surgical robot according to an embodiment of the present application.

Taking using surgical probe to collect at least three points on a patient anatomical structure as an example, the minimum unit of the registration algorithm is a triangle. Assuming that the points marked by the surgeon during the surgery are three points A, B and C, and the corresponding preoperative planed points are a, b and c. It can be assumed that the points marked by the surgeon are all on a surface of human tissue, and then we need to find three points a', b' and c' in a neighborhood of a, b and c, where the triangle ABC and the triangle a' b' c' are congruent and the three points a', b' and c' are all on the surface of human tissue. As such, the points a', b' and c' and the points A, B, and C on the human tissue have a high overlapping degree in positions since triangles have uniqueness. FIG. 14 is a schematic diagram of a registration process of a navigation and positioning system for a joint replacement surgical robot according to an embodiment of the present application. As shown in FIG. 14, on a left side of FIG. 14, points A, B, C are the points marked by the surgeon during the surgery, while on a right side of FIG. 14, points a, b, c are the points planned before the surgery. It can be seen that (A, B, C) and (a, b, c) have significant spatial positional errors. The blank points on the right side are points sets in the neighborhood of a, b, and c. The points a', b', and c' are selected from a large number of blank points, and the triangle a' b' c' composed of the three points a', b' and c' and the triangle ABC composed of the three points A, B and C are basically congruent triangles. At this time, the spatial positions of the preoperative planed points a, b and c are corrected to the spatial positions of a', b' and c', and then the points marked during the surgery and the preoperative planed points may be registered using iterative closest point (ICP) registration mode to achieve accurate registration for the femoral side surface and acetabular side surface.

It should be noted that due to the uniqueness and sufficient stability of a triangle, the triangle is used as the minimum registration unit during registration may effectively improve the accuracy of registration, thus achieving accurate registration for the femoral side surface and acetabular side surface.

In the embodiment, after the femoral side surface and acetabular side surface are accurately registered, the mechanical arm is manipulated to positioning the bone. The mechanical arm completes the operation in combination with accompanying surgical tools, ensuring accurate operation of hip joint replacement. At the same time, intraoperative adjustments may be made to the surgical scheme, breaking through limitations of traditional surgical tools, achieving personalized design for the patients, and completing prosthetic replacement to restore natural joint movement. In an embodiment, an end effector of the mechanical arm is moved to the surgical position on the bone of the patient and the end effector is controlled to perform osteotomy, rasion, and press-fitting operations on the hip joint based on the navigation instructions, as shown in FIGS. 9, 10, 11, and 12, where the navigation instructions match with the surgical scheme made by the preoperative planning module 1.

In the embodiment, a robot body associated with the mechanical arm control module 3 includes a movable base, a seven degree of freedom mechanical arm, and a robot end effector. The movable base is used as a base for an entire device. The seven degree of freedom mechanical arm is fixedly mounted above the movable base, and connected to a controller through a signal cable to receive control signals. The robot end effector is fixedly installed on a mechanical interface at an end of the mechanical arm and connected to the controller through wires to receive the control signals. The robot end effector is used as an operating tool of the robot, including a surgical bone saw, a surgical bone drill, and a surgical clamping tool.

In the embodiment, performance indicators include positioning error, repeated positioning accuracy, distance measurement error of the mechanical arm, operating range of the mechanical arm, the mechanical arm displacement under load, movement of the mechanical arm head when subjected to force, software functions (including patient sequence management, 3D browsing, image registration, 3D reconstruction, surgical scheme formulation, patient registration, and intraoperative orientation and positioning), which may assist in completing orthopaedic surgery for hip joint replacement, and completing operations such as osteotomy, rasion, and fixation.

According to the contents of the above-mentioned embodiments, in an embodiment, in case that a rasion operation is performed, the mechanical arm control module is used to:

determine a safe operating range and a conical stereotactic boundary; and when an operation position of the mechanical arm exceeds the safe operating range, control force exertion to generate the conical stereotactic boundary to control the mechanical arm to rasp within the conical stereotactic boundary;

where the conical stereotactic boundary appears when an acetabular rasp moves close to a planned position of an acetabular shell in an acetabulum, the boundary is designed to be of a specific conical shape, a cross section of the boundary is displayed to restrict the mechanical arm when the acetabular rasp moves close to a target position; when the acetabular rasp deviates from the conical stereotactic boundary, the acetabular rasp is guided back inside the conical stereotactic boundary; when the mechanical arm is used in the conical stereotactic boundary, the mechanical arm operates according to an coaxial within a positioning control range (the coaxial may effectively ensure consistency and safety of surgical operations); the mechanical arm supports power to complete high-speed rasion operations; in case that the mechanical arm moves beyond the conical stereotactic boundary by a preset angle, an electric source of the acetabular rasp is cut off to stop the rasion operation.

Figure 12:
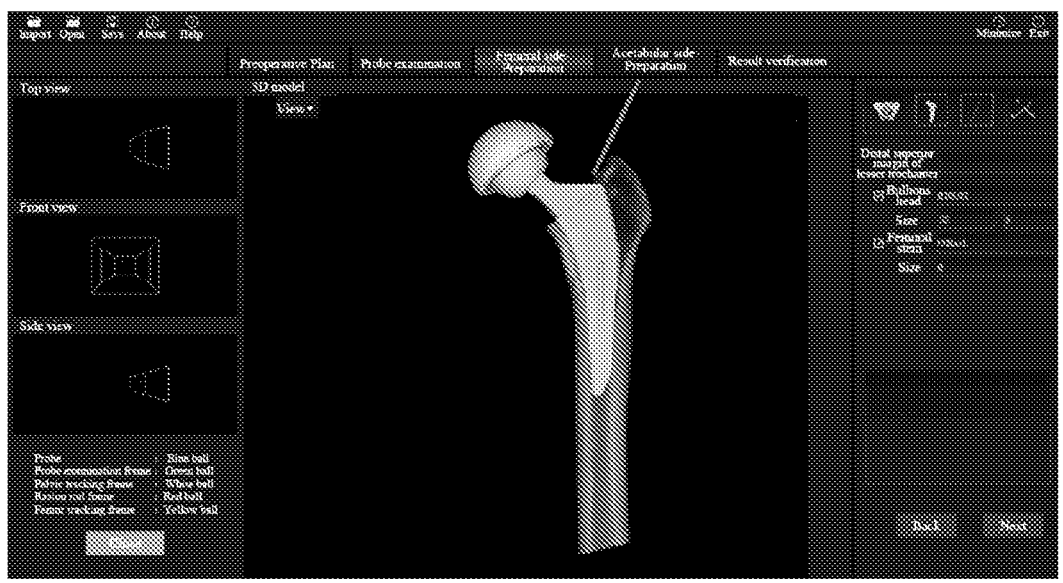
FIG. 12 is a schematic diagram of a safe rasion operation within a conical stereotactic boundary using another navigation and positioning system for a joint replacement surgical robot according to an embodiment of the present application.

In the embodiment, visual rasion is performed on the acetabular side under the guidance of a mechanical arm to preserve bone mass and reduce bleeding. As shown in FIG. 12, the system has set up a safe operating range and a stereotactic boundary to guide the operation of the mechanical arm. If the user attempts to operate outside of the safe operating range, the system may have a force exertion to generate a conical barrier (stereotactic boundary). The boundary automatically appears when the acetabular rasp moves close enough to the position of the planned acetabular shell in the acetabulum, and the boundary is designed to be of a specific shape. The cross section of the boundary is displayed to restrict the mechanical arm when the acetabular rasp moves close to the target position. When deviating from the stereotactic boundary, the acetabular rasp is guided back inside the planned boundary under the guidance of the system. When the mechanical arm is used in the stereotactic boundary, the mechanical arm completes the operation according to the coaxial within the positioning control range. The mechanical arm supports power to complete high-speed rasion operations. If the mechanical arm moves out of 5° beyond the range of positioning control, the electric source of the acetabular rasp is cut off to stop the rasion operation. In case that the stereotactic boundary is not used, users may perform rasion operation at any tilt and deflection angle. It can be seen that the embodiment of the present application constrains the operation process of the mechanical arm through the conical stereotactic boundary, effectively ensuring the safety of surgical operations through the mechanical arm. The embodiment of the present application may greatly reduce damage to soft tissues and bone tissues, resulting in less bleeding and minimal trauma for patients, and faster postoperative recovery of hip joint function.

In an embodiment, the angle range of the conical stereotactic boundary is approximately 10-15°, where the angle refers to an angle deviation from the acetabular axis, which ensures patient safety.

According to the contents of the above-mentioned embodiments, in the embodiment, in case that the mechanical arm control module performs a press-fitting operation, the mechanical arm control module is used to:

in case that the press-fitting operation is performed on the acetabulum and a pressing-fitting rod is moved into the acetabulum, the conical stereotactic boundary starts, the anteversion angle and the abduction angle are aligned in real time to make the anteversion angle and the abduction angle match with preoperative planed anteversion angle and abduction angle respectively, and a matching effect is displayed; and the press-fitting operation is stopped when a distance between a head end of the acetabular rasp and a target depth is 0 mm in each direction of an upper and lower direction, an inner and outer direction and a forward and backward direction, while a press-fitting map and the conical stereotactic boundary are updated.

In the embodiment, under the guidance of the mechanical arm, the position of the acetabular shell is positioned to assist the surgeon in accurate implantation through visual effects and force feedback. In case that the the press-fitting operation is performed on the acetabulum and the pressing-fitting rod is moved into the acetabulum, the conical stereotactic boundary starts, and the mechanical arm control module aligns the anteversion angle and the abduction angle in real time to make the anteversion angle and the abduction angle match with the preoperative planed anteversion angle and the preoperative planed abduction angle respectively, and the matching effect is displayed (e.g., the anteversion angle is 20°, and the abduction angle is 40°). The press-fitting operation is stopped when the distance between the head end of the acetabular rasp and the target depth is 0 mm in each direction of the upper and lower direction, the inner and outer direction and the forward and backward direction. And the system updates the press-fitting map and the stereotactic boundary at the same time. In case of the user's operation, the intraoperative navigation system may monitor whether the patient moves in real time, and in case that the patient moves, the mechanical arm performs position compensation in real time, and provide a guidance to assist the surgeon in completing the operation in a compensation mode. In the present application, the mechanical arm is a 7 degree of freedom movable joint and has two states during the operation process. In a "free arm" state, the mechanical arm may move freely without constraints and is not limited by the stereotactic boundary. In a "fixed arm" state, the mechanical arm moves within a preset range, which provides a safe resting state for the mechanical arm, and has more resistance compared to the free arm. At the same time, the system is equipped with multiple control and protection mechanisms. The display screen displays the effect of press-fitting operation in real time to guide the user to operate and set a boundary protection, where the anteversion angle is 20°, and the abduction angle is 40°. A power of the model may automatically stop and provide sound prompts within the boundary protection range. At the same time, the system may support users to complete emergency stop, mechanical protection, power outage protection and other functional operations.

In the embodiment, the navigation and positioning system may also include the following parts—a mechanical arm system, an optical navigation and positioning system, a computer control system, and supporting auxiliary tools. Real time positioning and operation of the mechanical arm under optical navigation may be achieved through the "mechanical arm and navigation" mode. A full space coordinate conversion technology of robot assisted navigation system is studied, and the scheme of transforming planned tools in the image into a patient bone coordinate system is also studied. A mapping relationship between the patient bone coordinate system and the robot-based coordinate system is established based on an optical positioning system, thereby establishing the transformation from the image coordinate system to the robot-based coordinate system. In an embodiment, an image of the injured position of the patient is obtained before/during surgery and is uploaded to a main console for identification. The surgeon plans a surgical path design through the main console. After the surgeon drags the mechanical arm to a surgical area, the mechanical arm performs accurate positioning according to the planned surgical path and completes the intraoperative operation. In the embodiment, the computer system may reconstruct and segment CT data to complete preoperative planning. At the same time, the computer system has a capability of automatically recognizing mark points on a body surface feature in 3D images, and achieves coordinate mapping in patient space, robot space, and image space by registering the mark points. The motion control algorithm of a seven degree of freedom mechanism is used to control the robot motion, where the motion control algorithm includes fast positioning point control algorithm and accurate trajectory control algorithm. The motion trajectory planning of robot may be adjusted based on a preset reference position. Optical navigation and positioning systems are generally composed of computer software such as measuring instruments, sensors, and optical locators. In modeling and planning stage, through the imaging system, image collection, processing, and feature analysis are completed, and the surgical implementation strategy is determined. In this stage, the operation of the surgery is mainly ensured by the navigation and positioning of the robot. In the embodiment, a central control module of the computer system is connected to the optical tracking system through a local area network, receives the navigation instruction from the navigation device, and outputs information such as robot position and posture to the optical tracking system. The central control module is connected to a multi axis motion control module through a PCI bus. The central control module completes the motion planning for the robot and sends instructions to the multi axis motion control module, and the multi axis motion control module implements the motion control for the robot. The mechanical arm is a multi-degree of freedom arm, and by using the mechanical arm in combination with specialized surgical instruments, an entire space range associated with a total hip replacement surgery is covered according to preoperative planed parameters without machine position change, which achieves accurate positioning.

In the embodiment, the surgical assistant robot in the embodiment of the present application may autonomously implement preoperative planed operations, and may be adjusted by the surgeon at any time during the surgery. The positioning for the mechanical arm is accurate, stable, and powerful, which may avoid fatigue and arm tremors of the surgeon caused by prolonged manual surgery, thereby improving the accuracy, stability, and safety of the surgery. In addition, the embodiment of the present application has high degrees of freedom and strong applicability. The traditional orthopedic surgical assistant robot systems are designed for specific surgical operations, while the surgical assistant robot in the embodiment of the present application has 7 degrees of freedom, high flexibility, and redundant degrees of freedom, making it easy to collaborate with surgeon for operations.

In the embodiment, fast interface technology (data interface and mechanical interface) is used between functional modules to facilitate the assembly of frameworks and the connection of a drive motor and a cable.

In the embodiment, a control structure including upper computer and lower computer may be used, where the upper computer uses a computer system to send motion control instructions to the lower computer based on the preoperative planning content, and the lower computer is a 7-degree of freedom mechanical arm that receives control instructions from the upper computer to achieve robot connection and motion. Two different control modes including automatic control mode and manual control mode are used in the system control. When the automatic control mode is used, the computer system is used as the upper computer to complete human-machine interaction with the surgeon and send control information to the lower robot. When the manual control mode is used, the manual control panel is used as the upper computer, and the surgeon directly controls the movements of the navigation unit and traction unit through buttons. This design achieves redundancy in the control system. Under normal circumstances, the computer system may be used to automatically control the movements of the navigation unit and robot positioning unit. Once the computer system malfunctions, a manual control panel may be used, which improves the reliability and stability of the control system.

In the embodiment, the control structure is open and may be integrated with the navigation system as a basic platform. The operation mode is flexible, which may be connected to an automatic navigation device and used as an executing mechanism to complete preoperative planed operations under the guidance of the navigation device. It can also be used as an independent surgical auxiliary instrument to implement surgical operations such as osteotomy and rasion under the operation of the surgeon, thereby greatly improving the quality of real-time tracking data flow and anti-shaking function.

Figure 15:
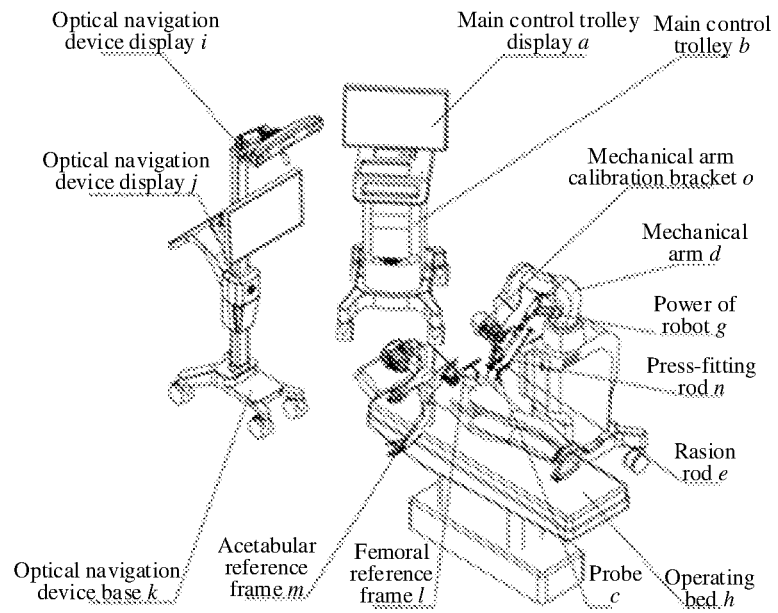
FIG. 15 is a schematic diagram of an application scenario of an orthopedic surgical robot according to an embodiment of the present application.
Figure 16:
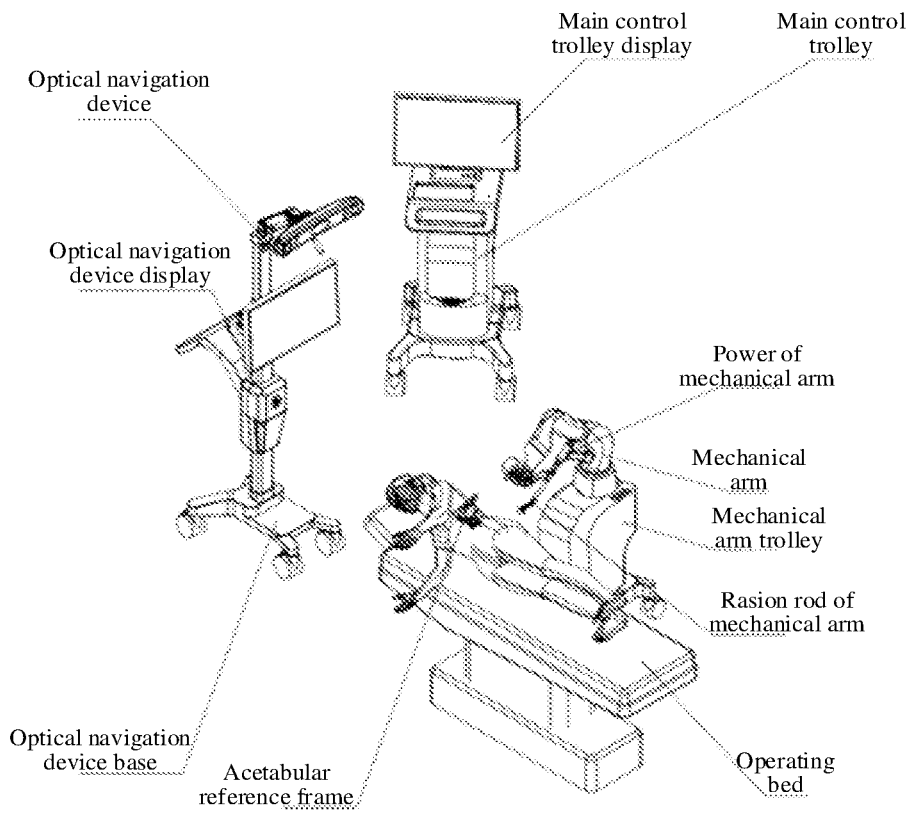
FIG. 16 is a schematic diagram of a rasion scenario of a navigation and positioning system for a joint replacement surgical robot according to an embodiment of the present application.
Figure 17:
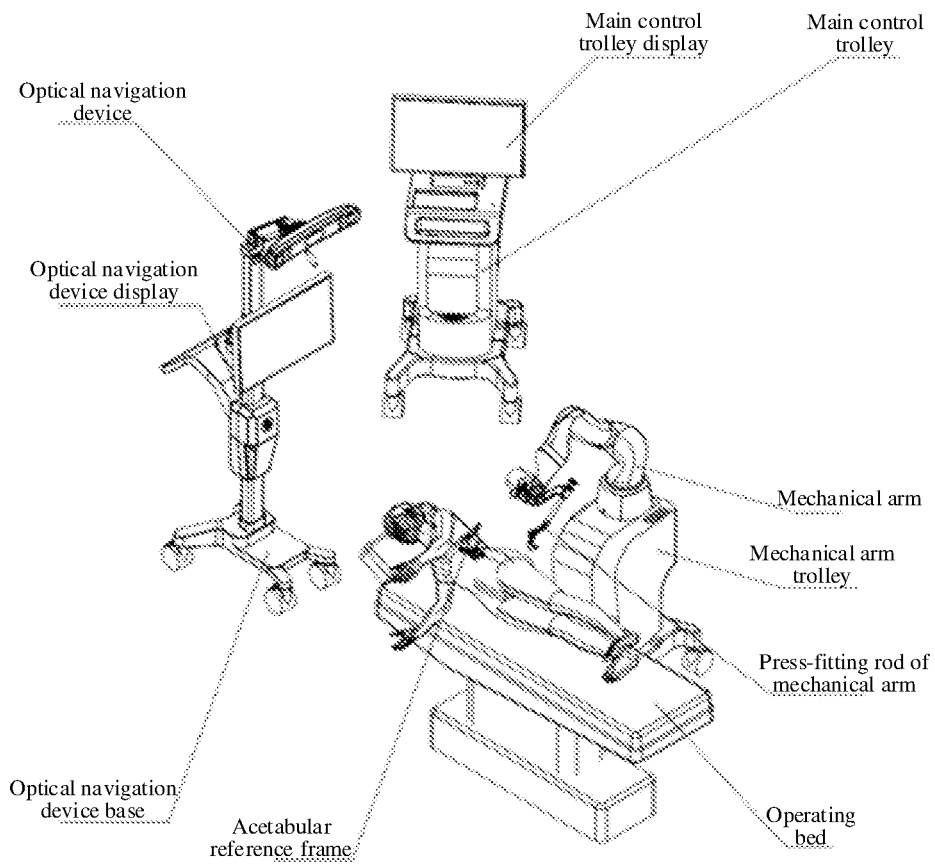
FIG. 17 is a schematic diagram of a press-fitting scenario of a navigation and positioning system for a joint replacement surgical robot according to an embodiment of the present application.

FIG. 15 illustrates a schematic diagram of an application scenario of an orthopedic surgical robot according to an embodiment of the present application. As shown in FIG. 15, a represents a main control trolley display, which is used to complete preoperative planning and display real-time information of the entire surgical process; b represents the main control trolley, which is used to carry the main control trolley display a and may move freely; i represents an optical navigator used to track the spatial positions of the mechanical arm d, a probe c, a femoral reference frame 1, and an acetabular reference frame m; c represents a surgical probe, which is used to collect some points on the anatomical structure of the patient; d represents the mechanical arm of an orthopedic surgical robot, which is a 7-degree of freedom mechanical arm fixed above a movable base and connected to the controller through a signal cable to receive the control signal from the controller; e represents the rasion rod, which is used to implement the rasion operation through the mechanical arm d; f represents a calibration bracket of the mechanical arm, which is used to carry the mechanical arm d; g represents a mechanical arm power, which may move based on the force direction of the head end to complete operations such as osteotomy and fixation; h represents an operating bed, which is used to carry surgical patients; m represents the acetabular reference frame, which is used to locate the acetabular side position of the patient; 1 represents the femoral reference frame, which is used to locate the femur position of the patient; j represents the optical navigator display, which is used to display the spatial postures of the mechanical arm d, the probe c, the femoral reference frame 1, and the acetabular reference frame m captured by the optical navigator i; k represents the optical navigation base, which is used to carry the optical navigator i and the optical navigator display j and may move freely. As shown in FIGS. 16 and 17, in the embodiment of the present application, the rasion operation is firstly performed, and then the press-fitting operation is performed.

Figure 13:
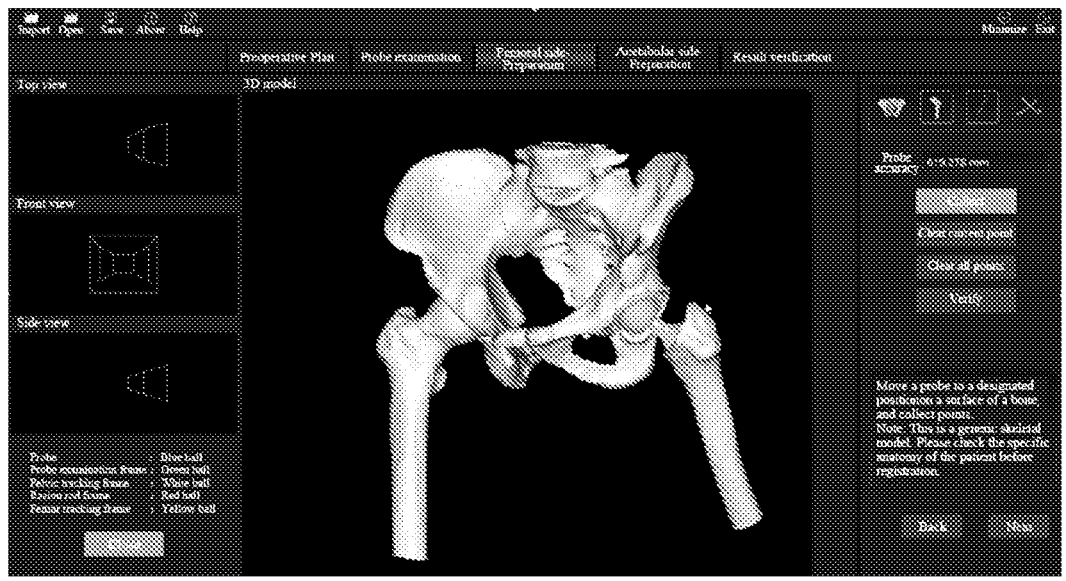
FIG. 13 is a schematic diagram of a reduction operation of a navigation and positioning system for a joint replacement surgical robot according to an embodiment of the present application.

In the embodiment, the navigation and positioning system for the joint replacement surgical robot further includes a reduction determining submodule, which is used to determine, after the prosthesis is planted, whether a reduction operation needed to be performed. Referring to FIG. 13, FIG. 13 illustrates a schematic diagram of a reduction operation of a navigation and positioning system for a joint replacement surgical robot according to an embodiment of the present application.

Embodiments of the present application provide a navigation and positioning system for a joint replacement surgical robot. Before the surgery, the 3D model of the hip joint is obtained based on the medical image data of the hip joint, and then preoperative planning is performed based on the 3D model of the hip joint to determine the surgical scheme. During the surgery, the navigation instruction is generated according to the surgical scheme, and the 3D model of the hip joint is registered based on the spatial position relationship between the hip joint of the patient and the surgical probe, therefore a structure of the hip joint of the patient may be accurately reflected through the 3D model of the hip joint, so that the surgical position on the bone of the patient may be accurately located, and the surgical robot may perform surgical operations according to the navigation instruction and surgical position. It can be seen from the above-mentioned description that the embodiments of the present application uses the 3D model for preoperative planning, uses the spatial positioning methods for intraoperative navigation and positioning, so that the surgical robot may optimize surgical path planning by using the high-accuracy 3D model, and realize the surgical path through a high degree of freedom mechanical arm, thereby assisting orthopedic surgeons in completing operations such as osteotomy, grinding, and fixation. The embodiment of the present application may improve surgical success rate and also may greatly reduce damage to soft tissues and bone tissues, resulting in less bleeding and minimal trauma for patients, and faster postoperative recovery of hip joint function.

According to contents of the above-mentioned embodiment, the optical navigation and positioning module is used to:

determine a spatial position of the hip joint of the patient according to a pelvic reference frame and a femoral reference frame; register the three-dimensional model of the hip joint to obtain the hip joint entity model based on a spatial position relationship between the hip joint of the patient and a mechanical arm, and determine the surgical position on the bone of the patient and a real-time position and posture of the mechanical arm according to the hip joint entity model.

Figure 2:
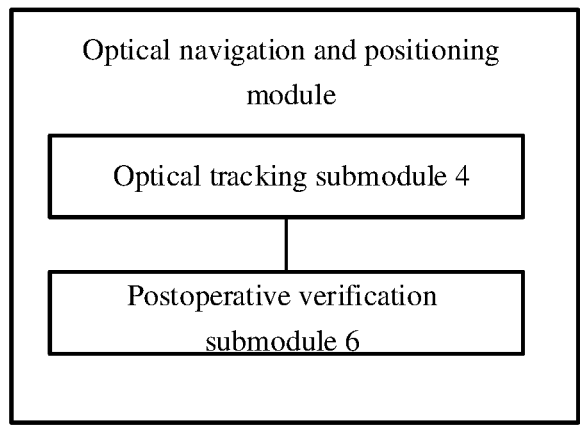
FIG. 2 is a schematic structural diagram of an optical positioning module of a navigation and positioning system for a joint replacement surgical robot according to an embodiment of the present application.

In the embodiment, FIG. 2 illustrates a schematic structural diagram of an optical positioning module of a navigation and positioning system for a joint replacement surgical robot according to an embodiment of the present application. The pelvic reference frame and femoral reference frame may be manually placed on the acetabular side and femoral side, and a navigation camera of the system may be used to track tracer elements on the pelvic reference frame and femoral reference frame to determine spatial positions of the pelvis and femur of the patient. Correspondingly, in case that the mechanical arm enters the tracking range of the navigation camera of the system, the spatial position of the mechanical arm is determined through the tracer elements on the mechanical arm, and then the spatial positions of the mechanical arm, pelvic reference frame, and femoral reference frame are integrated into a common coordinate system to register the 3D model of the hip joint. At this time, the posture and position information of the mechanical arm may be displayed in real time in the 3D model of the hip joint. It can be seen that in the embodiment of the present application, by comparing and calibrating the reference position of the surgical area obtained before/during surgery with the real-time position of the mechanical arm, a tracking and navigation to the mechanical arm may be achieved. The traditional hip joint replacement technology has a high degree of difficulty in registering the actual spatial position of the image and the actual bone tissue of the patient during surgery, thereby making it impossible to calibrate the position of the mechanical arm and resulting in positional errors of the mechanical arm.

Bone tissue is attached to the skin and muscles, and is located at a deeper depth, which are deep and difficult to fully expose during surgery. It is difficult for the naked eye to perform fluoroscopy, and in order to obtain accurate surgical positions, traditional surgery requires the use of multiple intraoperative CT scans, and by combining images, human eye observation, and surgeon experience, the surgical position may be determined, resulting in significant errors and heavy reliance on surgeon experience. Orthopedic robots need to compare and calibrate the reference position of the surgical area obtained before/during surgery with the real-time position of the surgical instruments, thereby achieving tracking and navigation to the surgical instruments.

According to contents of the above-mentioned embodiments, in the embodiment, the optical navigation and positioning module includes an optical tracking submodule 4:

the optical tracking submodule is used to register the hip joint entity model based on a spatial position relationship between the mechanical arm and the pelvic reference frame and the femoral reference frame, and calibrate positions of a mechanical arm model according to the registered hip joint entity model.

FIG. 15 is a schematic diagram of the calibration of a mechanical arm of a navigation and positioning system for a joint replacement surgery robot according to an embodiment of the present application. As shown in FIG. 15, after the 3D model of the hip joint is registered to obtain the hip joint entity model based on the spatial position relationship between the hip joint of the patient and the mechanical arm, and the surgical position on the bone of the patient and the real-time position and posture of the mechanical arm is determined according to the hip joint entity model, the position of the mechanical arm model is calibrated. The optical tracking submodule 4 is responsible for real-time positioning monitoring during the surgery, real-time dynamically adjusting positioning error, and guiding automatic adjustment of the mechanical arm. In the traditional technology, the navigation robot system cannot perform a fine-tuning to the surgical scheme and cannot break through the limitations brought by traditional surgical tools. It can be seen that the embodiment of the present application may calibrate the positions of the mechanical arm and surgical instruments, accurately calculate the coordinate system of different surgical instruments, and realize the identification of mark points and the conversion of different coordinate systems through software.

Figure 3:
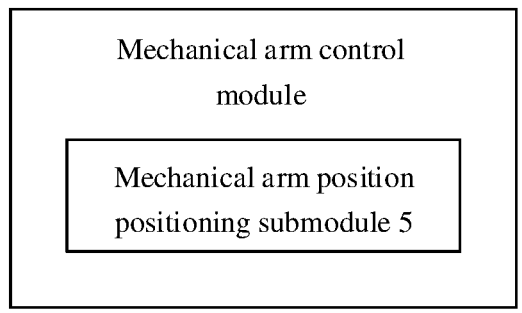
FIG. 3 is a schematic structural diagram of a mechanical arm control module of a navigation and positioning system for a joint replacement surgical robot according to an embodiment of the present application.

According to the contents of the above-mentioned embodiments, in the embodiment, FIG. 3 illustrates a schematic structural diagram of a mechanical arm control module of a navigation and positioning system for a joint replacement surgical robot according to an embodiment of the present application. The mechanical arm control module includes a mechanical arm position positioning submodule.

The mechanical arm position positioning submodule 5 is used to: send position and posture information of the mechanical arm to the optical tracking submodule to make the optical tracking submodule obtain spatial position information of the mechanical arm in real time.

In the embodiment, the mechanical arm position positioning submodule 5 may send the obtained position and posture information of the mechanical arm to the optical tracking submodule 4, so that the optical tracking submodule obtains the spatial position information of the mechanical arm in real time, so as to perform error calibration of the mechanical arm according to the spatial position information of the mechanical arm.

Figure 4:
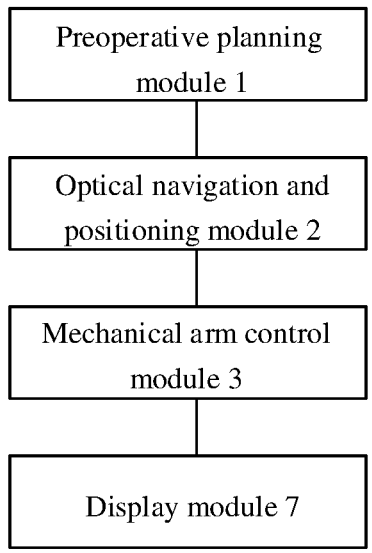
FIG. 4 is a schematic structural diagram of another navigation and positioning system for a joint replacement surgical robot according to an embodiment of the present application.

According to contents of the above-mentioned embodiments, in the embodiment, FIG. 4 illustrates a schematic structural diagram of another navigation and positioning system for a joint replacement surgical robot according to an embodiment of the present application. The navigation and positioning system for the joint replacement surgical robot further includes a display module 6.

The display module 6 is communicated with the optical navigation and positioning module 2 and configured to display a real-time states of the hip joint entity model on a human-computer interactive display screen.

In the embodiment, the display module 6 is used to display the real-time intraoperative states of the hip joint entity model on the human-computer interactive display screen, which is convenient for the reference and control of the surgeon.

According to contents of the above-mentioned embodiments, in the embodiment, the optical navigation and positioning module collects spatial positions of at least three mark points on the bone of the patient through the surgical probe to register the 3D model of the hip joint based on spatial position relationships between the at least three mark points on the bone of the patient and the hip joint of the patient to obtain the hip joint entity model.

In the present embodiment, a needle tip of the surgical probe is used to contact at least three different positions on the acetabular side and the femoral side during the operation, so that the femur in the 3D model of the hip joint may be registered according to the spatial position relationship between the at least three points on the femur anatomy structure collected by the surgical probe and the femoral reference frame. The acetabulum side in the 3D model of the hip joint may be registered according to the spatial position relationship between the at least three points on the acetabular side structure collected by the surgical probe and the pelvic reference frame.

According to the contents of the above-mentioned embodiments, in the embodiment, FIG. 4 illustrates a schematic structural diagram of another navigation and positioning system for a joint replacement surgical robot according to an embodiment of the present application. The navigation and positioning system for a joint replacement surgical robot further includes: a postoperative verification submodule 6.

The postoperative verification submodule 6 is used to, after the 3D model of the hip joint is registered, collect spatial positions of at least three mark points on the bone of the patient again through the surgical probe, and verify that whether the registered positions of the mark points are correct.

In the embodiment, after the registration for the acetabular side and femoral side is completed, the accuracy of the registration is verified based on a distance from the registered collection point to the bone surface.

Figure 5:
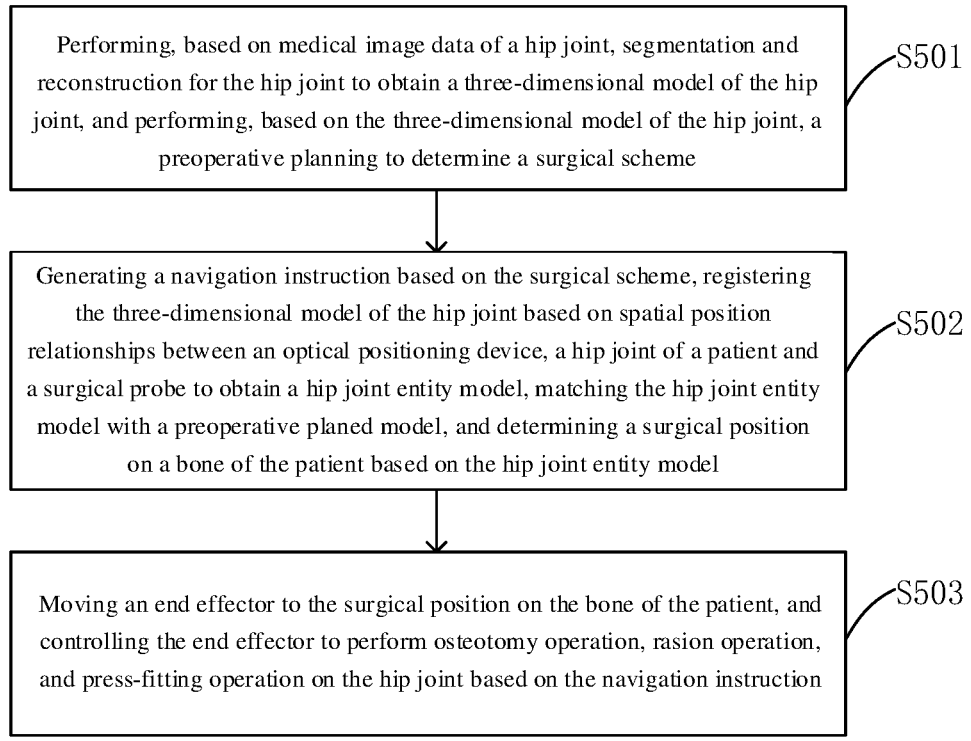
FIG. 5 is a schematic flowchart of a navigation and positioning method for a joint replacement surgical robot according to an embodiment of the present application.
Figure 6:
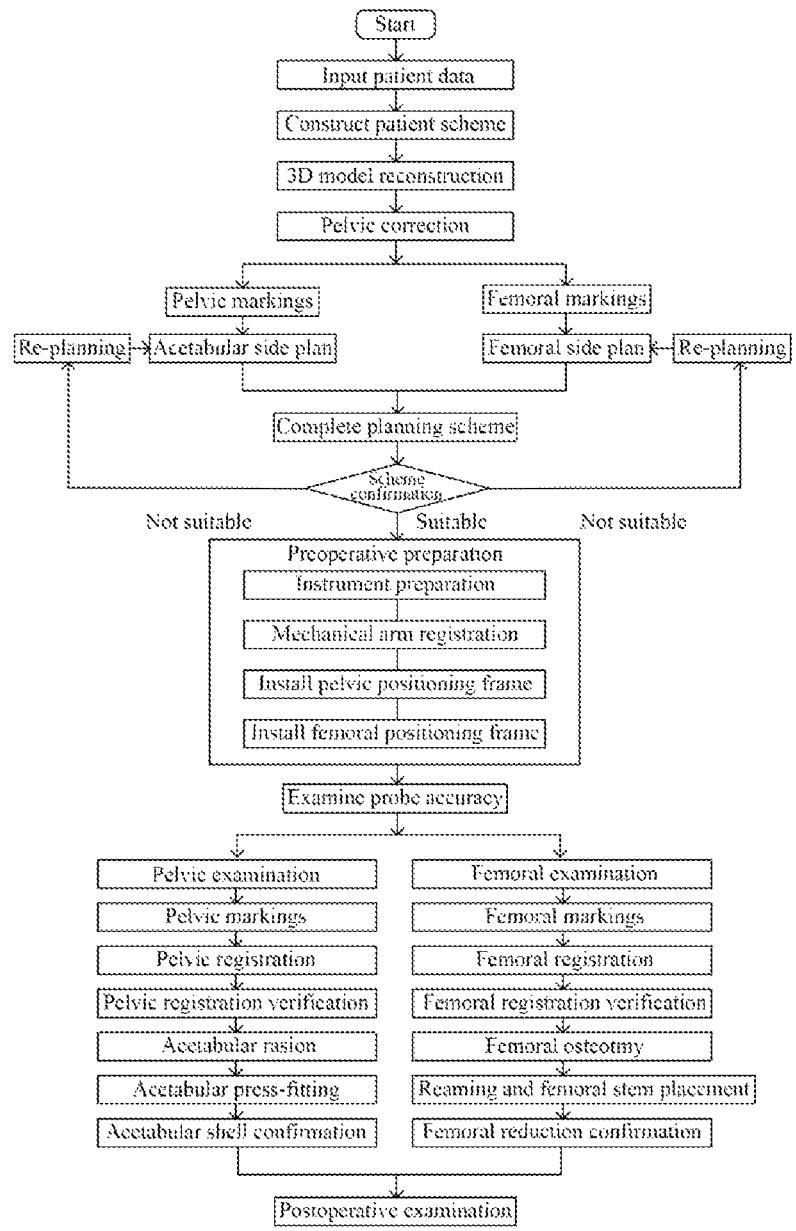
FIG. 6 is a schematic flowchart of another navigation and positioning method for a joint replacement surgical robot according to an embodiment of the present application.

Based on the same invention idea, another embodiment of the present application provides a navigation and positioning method for a joint replacement surgical robot. FIG. 5 is a schematic flowchart of a navigation and positioning method for a joint replacement surgical robot according to an embodiment of the present application, and FIG. 6 is a schematic flowchart of another navigation and positioning method for a joint replacement surgical robot according to an embodiment of the present application. The navigation and positioning method includes the following steps.

Step 501: performing, based on medical image data of a hip joint, segmentation and reconstruction for the hip joint to obtain a three-dimensional model of the hip joint, and performing, based on the three-dimensional model of the hip joint, a preoperative planning to determine a surgical scheme.

In step 501, preoperative scanning on pelvis and lower limbs of a patient may be performed by using imaging devices (such as CT/MRI/X-ray) to generate a preoperative 3D view of the pelvis and lower limbs. In an embodiment, before a surgery, the surgical navigation system reads a CT image with a DICOM format, segments a hip joint image to obtain multiple segmented images, and reconstructs, based on image data corresponding to the multiple segmented images, an individualized complex 3D model of the hip joint, where the 3D model of the hip joint includes a virtual pelvis and femur, which makes the surgeon comprehensively evaluate preoperative conditions of the patient through the 3D model of the hip joint, plan the surgical scheme using a system software, and simulate the surgical scheme for the hip joint (femoral and acetabular sides). The surgical scheme includes surgical information of an implanted prosthesis, such as a position, a size and an angle. In the embodiment of the present application, a medical image processing may be implemented on a common computer, and surgeons may arbitrarily divide visualized 3D images. In the surgical navigation system, lesion information is clearly visible and easy to surgical operation.

Step 502: generating a navigation instruction based on the surgical scheme, registering the three-dimensional model of the hip joint based on spatial position relationships between an optical positioning device, a hip joint of a patient and a surgical probe to obtain a hip joint entity model, matching the hip joint entity model with a preoperative planed model, and determining a surgical position on a bone of the patient based on the hip joint entity model.

In step 502, pelvic reference frame and femoral reference frame may be manually placed on the acetabular side and femoral side respectively, and tracer elements on the pelvic reference frame and femoral reference frame may be tracked by using a navigation camera of the system to determine spatial positions of the pelvis and femur of the hip joint of the patient. Correspondingly, in case that the surgical probe collects points, the navigation camera tracks a tracer element at a tail of the surgical probe, calculates spatial positions of the collected points through an algorithm, and then integrates the spatial positions of the surgical probe, pelvic reference frame and femoral reference frame into a common coordinate system to register the 3D model of the hip joint. At this time, the corresponding collection points may be displayed in the 3D model of the hip joint, and accurate registration for the femoral side surface and acetabular side surface may be achieved through a point cloud registration algorithm. A coordinate system between intraoperative patient positions and preoperative scanning data (such as CT and MRI) is registered to find a conversion relationship between the preoperative scanning data and the intraoperative patient position, and then the 3D model of the hip joint generated in the preoperative plan may be corrected based on the intraoperative patient position to reduce spatial position errors of mark points in the preoperative planning process, thereby greatly improving the registration accuracy.

Step 503: moving an end effector to the surgical position on the bone of the patient, and controlling the end effector to perform osteotomy operation, rasion operation, and press-fitting operation on the hip joint based on the navigation instruction.

In the step 503, after the femoral side surface and acetabular side surface are accurately registered, the mechanical arm is manipulated to positioning the bone. The mechanical arm completes the operation in combination with accompanying surgical tools, ensuring accurate operation of hip joint replacement. At the same time, intraoperative adjustments may be made to the surgical scheme, breaking through limitations of traditional surgical tools, achieving personalized design for the patients, and completing prosthetic replacement to restore natural joint movement. In an embodiment, an end effector of the mechanical arm is moved to the surgical position on the bone of the patient and the end effector is controlled to perform osteotomy, rasion, and press-fitting operations on the hip joint based on the navigation instructions. The navigation instructions match with the preoperative planning surgical scheme.

Embodiments of the present application provide a navigation and positioning method for a joint replacement surgical robot. Before the surgery, the 3D model of the hip joint is obtained based on the medical image data of the hip joint, and then preoperative planning is performed based on the 3D model of the hip joint to determine the surgical scheme. During the surgery, the navigation instruction is generated according to the surgical scheme, and the 3D model of the hip joint is registered based on the spatial position relationship between the hip joint of the patient and the surgical probe, therefore a structure of the hip joint of the patient may be accurately reflected through the 3D model of the hip joint, so that the surgical position on the bone of the patient may be accurately located, and the surgical robot may perform surgical operations according to the navigation instruction and surgical position. It can be seen from the above-mentioned description that the embodiments of the present application uses the 3D model for preoperative planning, uses the spatial positioning methods for intraoperative navigation and positioning, so that the surgical robot may optimize surgical path planning by using the high-accuracy 3D model, and realize the surgical path through a high degree of freedom mechanical arm, thereby assisting orthopedic surgeons in completing operations such as osteotomy, grinding, and fixation. The embodiment of the present application may improve surgical success rate and also may greatly reduce damage to soft tissues and bone tissues, resulting in less bleeding and minimal trauma for patients, and faster postoperative recovery of hip joint function.

The navigation and positioning method for the joint replacement surgical robot described in the present embodiment may be used to perform the above system embodiment, and its principle and effects are similar, which are not repeated in the present application.

Figure 18:
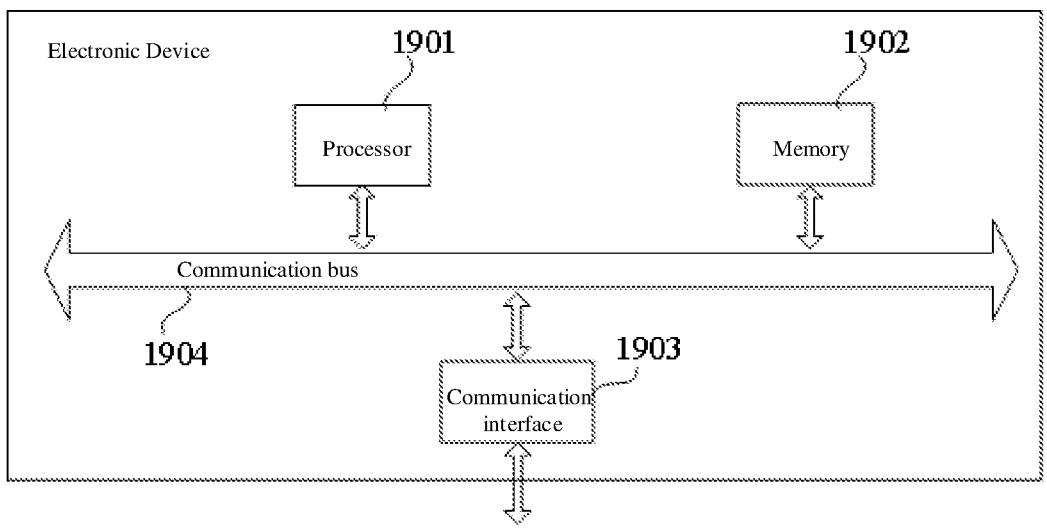
FIG. 18 is a schematic structural diagram of an electronic device according to an embodiment of the present application.

Based on the same invention idea, an embodiment of the present application provides an electronic device. Referring to FIG. 18, FIG. 18 illustrate a schematic structural diagram of an electronic device, including: a processor 1901, a memory 1902, a communication interface 1903 and a communication bus 1904.

The processor 1901, memory 1902, communication interface 1903 communicate with each other through the communication bus 1904. The communication interface 1903 is used to achieve information transmission between various devices.

The processor 1901 is used to call the computer program in the memory 1902, and when executing the computer program, the processor implements all the steps of the navigation and positioning method for the joint replacement surgical robot described above. For example, the method includes: performing, based on medical image data of a hip joint, segmentation and reconstruction for the hip joint to obtain a three-dimensional model of the hip joint, and performing, based on the three-dimensional model of the hip joint, a preoperative planning to determine a surgical scheme; generating a navigation instruction based on the surgical scheme, registering the three-dimensional model of the hip joint based on spatial position relationships between an optical positioning device, a hip joint of a patient and a surgical probe to obtain a hip joint entity mode, matching the hip joint entity model with a preoperative planed model, and determining a surgical position on a bone of the patient based on the hip joint entity model; and moving an end effector to the surgical position on the bone of the patient, and controlling the end effector to perform osteotomy operation, rasion operation, and press-fitting operation on the hip joint based on the navigation instruction.

Based on the same invention idea, an embodiment of the present application provides a non-transitory computer-readable storage medium having stored thereon computer programs, where the computer programs, when executed by a processor, cause the processor to perform all steps of the navigation and positioning method for the joint replacement surgical robot. For example, the method includes: performing, based on medical image data of a hip joint, segmentation and reconstruction for the hip joint to obtain a three-dimensional model of the hip joint, and performing, based on the three-dimensional model of the hip joint, a preoperative planning to determine a surgical scheme; generating a navigation instruction based on the surgical scheme, registering the three-dimensional model of the hip joint based on spatial position relationships between an optical positioning device, a hip joint of a patient and a surgical probe to obtain a hip joint entity mode, matching the hip joint entity model with a preoperative planed model, and determining a surgical position on a bone of the patient based on the hip joint entity model; and moving an end effector to the surgical position on the bone of the patient, and controlling the end effector to perform osteotomy operation, rasion operation, and press-fitting operation on the hip joint based on the navigation instruction.

Further, the logic instructions in the above memory may be implemented in the form of a software functional unit and may be stored in a computer-readable storage medium when sold or used as a separate product. Based on this understanding, the solutions of the present application in essence, or the parts of the solutions of the present application that contribute to the related art or the parts of the solutions may be embodied in the form of a software product. The computer software product is stored in a storage medium, including a number of instructions to enable a computer device (may be a personal computer, server, or network device, etc.) to perform all or part of the steps of the method described in each embodiment of the present application. The aforementioned storage media include: USB flash disk, mobile hard disk, read-only memory (ROM), random access memory (RAM), disk or optical disk and other media that can store program code.

By describing the above embodiments, those skilled in the art may clearly understand that each embodiment may be implemented by software plus the necessary general hardware platform, of course, or only by hardware. Based on this understanding, the solutions of the present application in essence, or the parts of the solutions of the present application that contribute to the related art or the parts of the solutions may be embodied in the form of a software product. The computer software product is stored in a storage medium, such as ROM/RAM, disk or optical disk and other media, which store a number of instructions to enable a computer device (may be a personal computer, server, or network device, etc.) to perform the navigation and positioning method for the joint replacement surgical robot described in each embodiment or part of the embodiment of the present application.

Finally, it should be noted that the above embodiments are only used to illustrate the solutions of the present application, and are not limited thereto. Although the present application is described in detail with reference to the foregoing embodiments, those of ordinary skill in the art should understand that they may still modify the solutions described in each of the foregoing embodiments, or equivalently replace some of the features. These modifications or replacements do not depart the essence of the corresponding solutions from the scope of the solutions of each embodiment of the present application.

What is claimed is:

1. A navigation and positioning system for a joint replacement surgical robot, comprising: a preoperative planning module, an optical navigation and positioning module and a mechanical arm control module;
   wherein the preoperative planning module is configured to perform, based on medical image data of a hip joint of a patient, segmentation and reconstruction for the hip joint to obtain a three-dimensional model of the hip joint, and perform, based on the three-dimensional model of the hip joint, a preoperative planning to determine a surgical scheme;
   the optical navigation and positioning module is configured to generate a navigation instruction based on the surgical scheme, register the three-dimensional model of the hip joint based on spatial position relationships between an optical positioning device, a hip joint of a patient and a surgical probe to obtain a hip joint entity model, match the hip joint entity model with a preoperative planned model, and determine a surgical position on a bone of the patient based on the hip joint entity model;
   the mechanical arm control module is configured to move an end effector to the surgical position on the bone of the patient, and control the end effector to perform an osteotomy operation, a rasion operation, and a press-fitting operation on the hip joint based on the navigation instruction;
   wherein the preoperative planning module comprises: a data obtaining submodule, a three-dimensional model reconstruction submodule, an acetabular side plan determination submodule, a femoral side plan determination submodule and a plan scheme confirmation submodule;
   wherein the data obtaining submodule is configured to obtain the medical image data of the hip joint;
   the three-dimensional model reconstruction submodule is configured to perform, based on the medical image data of the hip joint, segmentation and reconstruction for the hip joint to obtain the three-dimensional model of the hip joint;
   the acetabular side plan determination submodule is configured to determine an acetabulum rotation center, an acetabulum diameter, an acetabulum anteversion angle and an acetabulum abduction angle based on the three-dimensional model of the hip joint, and determine a size and a position of an acetabular side prosthesis based on the acetabulum rotation center, the acetabulum diameter, the acetabulum anteversion angle and the acetabulum abduction angle when considering an acetabular shell coverage rate;
   the femoral side plan determination submodule is configured to determine a caput femoris rotation center, a femur marrow cavity shape, a femur marrow cavity anatomical axis and a femur collodiaphyseal angle based on the three-dimensional model of the hip joint, and determine a size and a position of a femoral side prosthesis based on the caput femoris rotation center, the femur marrow cavity shape, the femur marrow cavity anatomical axis and the femur collodiaphyseal angle when considering a leg length difference and a femoral combined offset; and
   the plan scheme confirmation submodule is configured to confirm whether an acetabular side prosthesis implantation plan determined by the acetabular side plan determination submodule and a femoral side prosthesis implantation plan determined by the femoral side plan determination submodule are suitable; in case that the acetabular side prosthesis implantation plan determined by the acetabular side plan determination submodule or the femoral side prosthesis implantation plan determined by the femoral side plan determination submodule is not suitable, the acetabular side plan determination submodule and/or the femoral side plan determination submodule are triggered to re-determine an acetabular side prosthesis implantation plan and a femoral side prosthesis implantation plan; and in case that the acetabular side prosthesis implantation plan determined by the acetabular side plan determination submodule and the femoral side prosthesis implantation plan determined by the femoral side plan determination submodule are suitable, the acetabular side prosthesis implantation plan determined by the acetabular side plan determination submodule and the femoral side prosthesis implantation plan determined by the femoral side plan determination submodule are used as preoperative planning schemes.

2. The navigation and positioning system of claim 1, wherein the optical navigation and positioning module is configured to:
   determine a spatial position of the hip joint of the patient based on a pelvic reference frame and a femoral reference frame, register the three-dimensional model of the hip joint, based on a spatial position relationship between the hip joint of the patient and a mechanical arm to obtain the hip joint entity model, and determine the surgical position on the bone of the patient and a real-time position and posture of the mechanical arm based on the hip joint entity model.

3. The navigation and positioning system of claim 2, wherein the optical navigation and positioning module comprises an optical tracking submodule;

the optical tracking submodule is configured to register the hip joint entity model based on a spatial position relationship between the mechanical arm and the pelvic reference frame and the femoral reference frame, and calibrate a position of a mechanical arm model based on a registered hip joint entity model.

4. The navigation and positioning system of claim 3, wherein if the optical tracking submodule registers the hip joint entity model based on the spatial position relationship between the mechanical arm and the pelvic reference frame and the femoral reference frame, the optical tracking submodule is configured to:

use a triangle as a minimum unit in a registration process, and if points marked by a surgeon during a surgery are A, B and C, corresponding preoperative planned points are a, b and c, wherein the points marked by the surgeon are on a surface of human tissue;

select a', b' and c' from neighborhood space point sets corresponding to a, b and c, wherein all three points a', b' and c' are on the surface of human tissue, and a triangle a'b'c' composed of the three points a', b' and c' and a triangle composed of the three points A, B and C are congruent triangles; and correct preoperative planned spatial positions of a, b and c to spatial positions of a', b' and c', and register the points marked during the surgery and the preoperative planned points by using a registration mode.

5. The navigation and positioning system of claim 1, wherein the mechanical arm control module comprises a mechanical arm position positioning submodule;

the mechanical arm position positioning submodule is configured to send position and posture information of a mechanical arm to the optical tracking submodule to make the optical tracking submodule obtain spatial position information of the mechanical arm in real time.

6. The navigation and positioning system of claim 1, wherein if the mechanical arm control module performs the rasion operation, the mechanical arm control module is configured to:

determine a safe operating range and a conical stereotactic boundary;

when an operation position of a mechanical arm exceeds the safe operating range, control force exertion to generate the conical stereotactic boundary to control the mechanical arm to rasp within the conical stereotactic boundary;

wherein the conical stereotactic boundary appears when an acetabular rasp moves close to a planned position of an acetabular shell in an acetabulum, the boundary is designed to be of a conical shape; when the acetabular rasp moves close to a target position, a cross section of the boundary is displayed to restrict the mechanical arm; when the acetabular rasp deviates from the conical stereotactic boundary, the acetabular rasp is guided back inside the conical stereotactic boundary; when the mechanical arm is used within the conical stereotactic boundary, the mechanical arm operates according to a coaxial within a positioning control range, wherein the mechanical arm supports power to complete high-speed rasion operations; if the mechanical arm moves beyond the conical stereotactic boundary by a preset angle, an electric source of the acetabular rasp is cut off to stop the rasion operation.

7. The navigation and positioning system of claim 6, wherein if the mechanical arm control module performs the press-fitting operation on the acetabulum and a pressing fitting rod is moved into the acetabulum, the mechanical arm control module is configured to:

start the conical stereotactic boundary, align the anteversion angle and the abduction angle in real time to make the anteversion angle and the abduction angle match with a preoperative planned anteversion angle and abduction angle, and display a matching effect;

wherein the press-fitting operation is stopped when a distance between a head end of the acetabular rasp and a target depth is 0 mm in each direction of an upper and lower direction, an inner and outer direction and a forward and backward direction, while a press-fitting map and the conical stereotactic boundary are updated; and real-time monitoring of whether the patient moves during the press-fitting operation is performed, and if the patient moves, the mechanical arm performs position compensation in real time, and a guidance is provided to assist in completing the operation in a compensation mode.

8. The navigation and positioning system of claim 1, further comprising: a display module;

the display module communicates with the optical navigation and positioning module and configured to display a real-time status of the hip joint entity model on a human-computer interactive display screen.

9. The navigation and positioning system of claim 1, wherein the optical navigation and positioning module collects spatial positions of at least three mark points on the bone of the patient through the surgical probe, and registers the three-dimensional model of the hip joint based on spatial position relationships between the at least three mark points on the bone of the patient and the hip joint of the patient to obtain the hip joint entity model.

10. The navigation and positioning system of claim 1, wherein the optical navigation and positioning module further comprises: a postoperative verification submodule;

the postoperative verification submodule is configured to, after the three-dimensional model of the hip joint is registered, collect spatial positions of at least three mark points on the bone of the patient through the surgical probe, and verify whether registered positions of the mark points are correct.

* * * * *